United States Patent [19]
Dean et al.

[11] Patent Number: 5,957,372
[45] Date of Patent: Sep. 28, 1999

[54] APPARATUS AND METHOD FOR ACCEPTING RETURN OF UNUSED MEDICAL ITEMS

[75] Inventors: David M. Dean, Burgettstown; R. Michael McGrady, Baden, both of Pa.

[73] Assignee: Diebold, Incorporated, North Canton, Ohio

[21] Appl. No.: 08/679,203

[22] Filed: Jul. 12, 1996

[51] Int. Cl.⁶ .................................................. B65D 91/00
[52] U.S. Cl. ........................ 232/43.1; 232/44; 232/1 D; 312/330.1; 364/479.01; 221/9
[58] Field of Search .................................. 232/43.1, 1 R, 232/1 D, 44, 47, 57; 312/35, 72, 45, 209, 330.1, 333, 249.11, 249.8; 364/479.01, 478.02, 478.01; 221/2, 9

[56] References Cited

U.S. PATENT DOCUMENTS

| | | |
|---|---|---|
| 527,239 | 10/1894 | Garfield . |
| 2,690,870 | 10/1954 | Harman . |
| 3,401,875 | 9/1968 | Bruhns . |
| 3,758,027 | 9/1973 | Morgan .............................. 232/41.1 X |
| 4,267,942 | 5/1981 | Wich, Jr. et al. . |
| 4,278,308 | 7/1981 | Gotberg . |
| 4,720,611 | 1/1988 | Ishii . |
| 4,896,024 | 1/1990 | Morello et al. . |
| 5,047,948 | 9/1991 | Turner . |
| 5,165,768 | 11/1992 | Zarrabi et al. . |
| 5,314,243 | 5/1994 | McDonald et al. ............ 312/249.11 X |
| 5,445,294 | 8/1995 | Gardner et al. . |
| 5,526,979 | 6/1996 | Mann ..................................... 232/47 X |
| 5,549,375 | 8/1996 | Pagliaccio . |
| 5,564,803 | 10/1996 | McDonald et al. . |

*Primary Examiner*—Terry Lee Melius
*Assistant Examiner*—William L. Miller
*Attorney, Agent, or Firm*—Ralph E. Jolke

[57] ABSTRACT

An apparatus for accepting return of unused medical items is part of a system (10) used for automated dispensing and tracking of medical items within a medical facility. The apparatus includes a return drawer (52) and a retrieve drawer (54) which are opened responsive to signals received from a display terminal (26) which is networked with a computer (12) which includes a database (14). The return drawer includes a pocket (74) therein. The pocket is accessible from outside of a housing (56) when the return drawer is moved to an open position. The pocket includes an opening (76). The pocket is closed by a trap door (78) when the return drawer is in the open position. Medical items to be returned (132) are placed in the pocket and the return drawer is closed. Upon the closing of the return drawer the trap door is moved to an open position by an actuator. The returned medical item passes from the pocket to a retrieve area (84) in the retrieve drawer. Medical items are stored in the retrieve area until the retrieve drawer is opened by a user authorized to retrieve items from said retrieve area. The opening of the return and retrieve drawers is controlled responsive to the input of data at the display terminal corresponding to information in records (16) in the database.

17 Claims, 13 Drawing Sheets

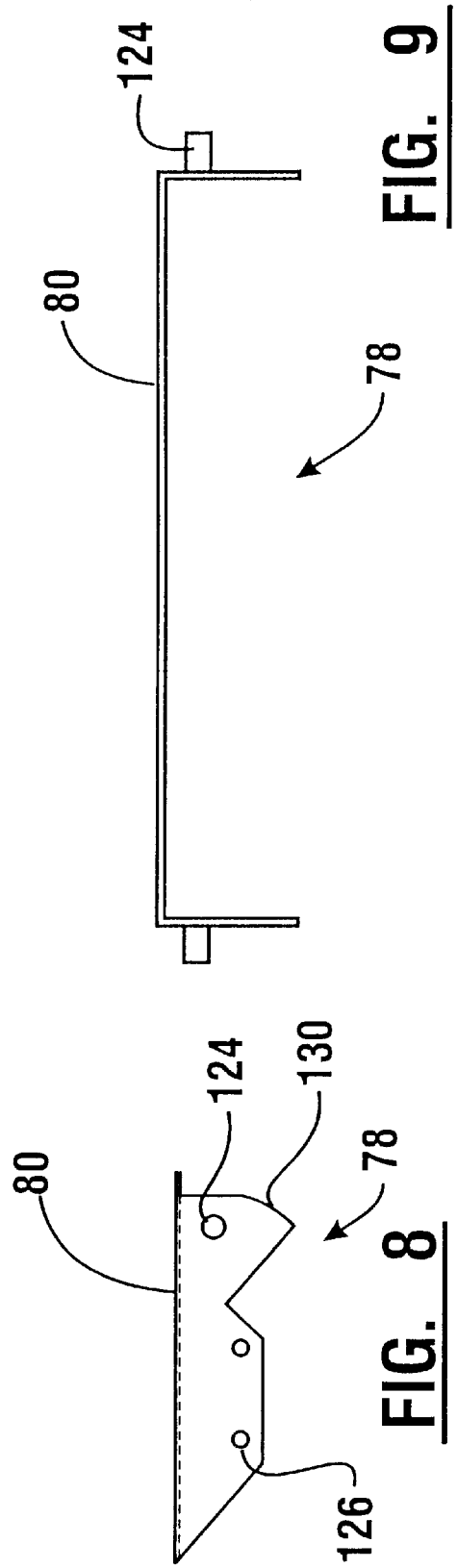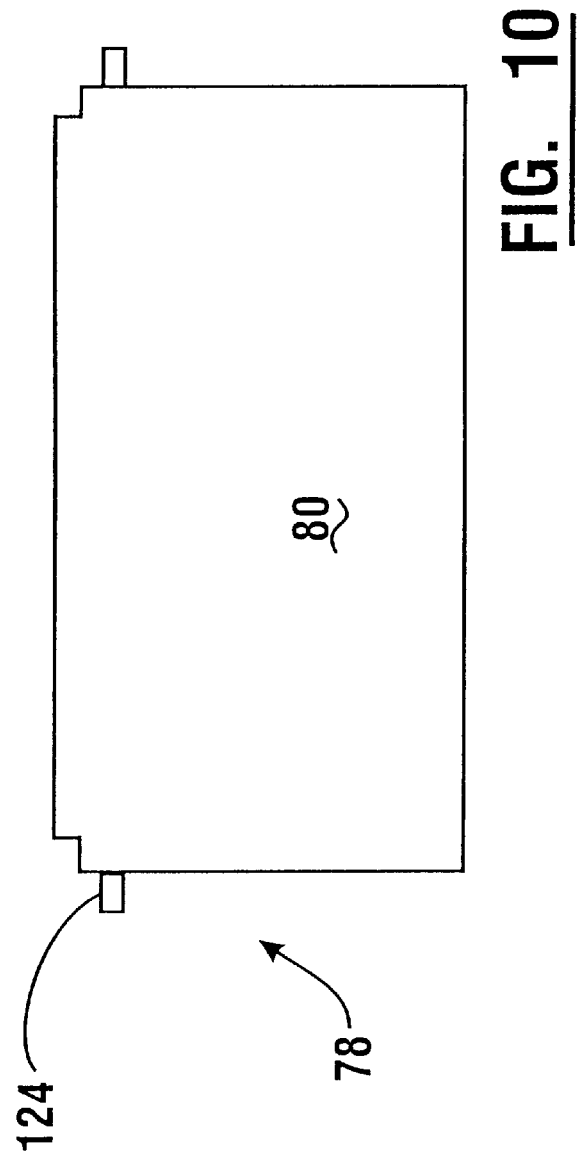

| Patient Information - [Shakespeare, William [0120002]Room:KDCUBE.Bed:2] |
|---|

| Patient ID | 0120002 | | Admitted | |
|---|---|---|---|---|
| Med Rec# | 900989 | | Date: | 1/23/96 |
| | | | Time: | 5:23:00 PM |

Patient Name: Shakespeare, Mr. William

Sex: M
Height: 5'.5"
Weight: 160
Date of Birth: 1/1/1675

Location
Room: KDCUBE
Bed: 2

Physician: Kachousky MD. Dr. Stanley P.
Allergies: Penicillin

[Help]   [Close]

| MedOrder - Browser - [ Shakespeare, William [0120002] Room: KDCUBE, Bed:2 ] |
|---|

| Generic Name | | CR | Order | Ordered Dose | Start Time | Review |
|---|---|---|---|---|---|---|
| Route | Freq | | Qty | Unit Dose | End Time | Check |
| AMOXICILLIN/CLAVULANA | | | 098007 | 5 gm | 07/10/96 12:15 | R |
| Intravenous | 8 hrs | | 1 | 100 TAB | 07/28/96 17:00 | C |

[Prev Page]  [Trade Name]  [Info]  [Dispense]  [Help]
[Next Page]                                      [Close]

| Patient Usage - Browser - [ Shakespeare, William [0120002] Room: KDCUBE, Bed:2 ] |||||
|---|---|---|---|---|
| Date / Time | Status | Generic Name | Qty | Size |
| 01-Jul 17:09 | Returned | BRETYLIUM | 1AMP | 1AMP |
| 01-Jul 17:07 | Taken | BRETYLIUM | 1 | 1AMP |

[Prev Page] [Trade Name] [Discrepancy] [Return] [Help]
[Next Page] [Waste] [Close]

Return Supply - [ Shakespeare, William [0120002] Room: KDCUBE, Bed:2 ]
Selected Supply: BRETYLIUM
Return Drawers
KD's Test Cabinet Drawer 2-1 R
KD's Test Cabinet 3-1 R

[Prev Page] [Trade Name] [Select] [Help]
[Next Page] [Close]

Return Amount - [ Shakespeare, William [0120002] Room: KDCUBE, Bed:2 ]

| Generic Name: | Size | Strength |
|---|---|---|
| BRETYLIUM | 1AMP | 500MG AMP |

Trade Name:
BRETYLOL

Return Reasons:   Returned Amount: 0 AMP

Another new reason

Cloudy
Dropped on floor
Looks Bad
Looks really bad
Patient died
Patient is sleeping
Patient is tired of taking med

[1] [2] [3] [Delete]
[4] [5] [6] [Clear]
[7] [8] [9]
[0]

[Prev Page] [Accept] [Help]
[Next Page] [Close]

Waste Supply - [ Shakespeare, William [0120002] Room: KDCUBE, Bed:2 ]

| Generic Name: | Size | Strength |
|---|---|---|
| BRETYLIUM | 1AMP | 500MG AMP |

Trade Name:
BRETYLOL

Wasting Reasons:   Wasted Amount: 1 AMP

Defective Container

Dropped/Broke

Expired

Patient Refused

[1] [2] [3] [Delete]
[4] [5] [6] [Clear]
[7] [8] [9]
[0]

[Prev Page] [Accept] [Help]
[Next Page] [Close]

| Retrieve Inventory | | | | |
|---|---|---|---|---|
| Return Drawer Inventory | | | | |
| Generic Name | Size | Strength | Qty in Units | |
| BRETYLIUM | 1AM | 500MG | 1AMP | |

| Prev Page | Trade Name | Discrepancy | Empty | Help |
|---|---|---|---|---|
| Next Page | | | Empty All | Close |

APPARATUS AND METHOD FOR ACCEPTING RETURN OF UNUSED MEDICAL ITEMS

TECHNICAL FIELD

This invention relates to systems for dispensing medical items. Particularly this invention relates to an apparatus for accepting the return of medical items that were previously dispensed and which were not used.

BACKGROUND ART

Medical dispensing systems are known in the prior art. Such systems are used for dispensing medications or other medical items to a health care provider or to a patient. Such systems also generally control the dispense of such items and track the use of medical items. An example of such system is shown in co-pending U.S. patent application Ser. No. 08/361,783 filed Dec. 16, 1994, now U.S. Pat. No. 5,790,409 and assigned to the assignee of the present invention. The disclosure of this Application is incorporated herein by reference.

In the use of systems for dispensing medical items it is possible to have a situation arise where an item previously taken for a patient is not used. In the system disclosed U.S. patent application Ser. No. 08/361,783, it is possible in some situations to return an item and to have the patient's account credited for the value of the item that has been returned. This is shown for medical items such as catheters.

When a medical item that has been previously dispensed and not used is a controlled substance, the return of such items must be carefully documented. The situation is further complicated where a portion of the medical item originally dispensed has been used. The unused portion must be accounted for and properly disposed of. It is also usually important to know why the entire dose of the substance dispensed was not used.

In the past, paper records were maintained concerning the return or waste of medical items. The item itself was also returned to the pharmacy or other department where it was matched up with the paper records to assure appropriate tracking.

Some unused medical items may be reused. This may occur when a medication has been refused by a patient or when the patient is transferred to another location prior to the medication being administered. In such circumstances there is no reason why the medication cannot be returned to inventory for dispense at a later date. However the tracking of the return as well as the crediting of the account of the patient for whom the medication was originally dispensed generally involves considerable effort.

Any unused medication that is a controlled substance must be held in a secure location until it can be taken by an authorized person. This is necessary to prevent pilferage or abuse. It is also desirable to avoid any confusion between the unused medications and other medications that are being prepared for administration to patients.

Thus there exists a need for an apparatus and method for accepting return of unused medical items, for holding such items in a secure location until they can be taken by an appropriate person, and for tracking the unused medical items and the circumstances associated with their return.

DISCLOSURE OF INVENTION

It is an object of the present invention to provide an apparatus for accepting the return of unused medical items.

It is a further object of the present invention to provide an apparatus for accepting return of unused medical items that holds such items securely until retrieved by an authorized person.

It is a further object of the present invention to provide an apparatus for accepting return of unused medical items which maintains previously returned items away from persons subsequently returning unused items.

It is a further object of the present invention to provide an apparatus for accepting return of unused medical items which maintains returned items in a compactly stored condition.

It is a further object of the present invention to provide an apparatus for accepting return of unused medical items that tracks the identities of persons returning such items.

It is a further object of the present invention to provide an apparatus for accepting return of unused medical items that limits those persons returning such items to authorized persons.

It is a further object of the present invention to provide an apparatus for accepting return of unused medical items that provides access to returned items only to authorized persons.

It is a further object of the present invention to provide an apparatus for accepting return of unused medical items that correlates the returned item with an item previously dispensed.

It is a further object of the present invention to provide an apparatus for accepting return of unused medical items that tracks an amount of such item wasted and the reasons the item is wasted.

It is a further object of the present invention to provide an apparatus for accepting return of unused medical items that enables crediting a patient's account for a returned item.

It is a further object of the present invention to provide an apparatus for accepting return of unused medical items that is reliable and economical.

It is a further object of the present invention to provide a method for accepting return of unused medical items.

It is a further object of the present invention to provide a method for accepting return of unused medical items that enables only authorized users to return such items.

It is a further object of the present invention to provide a method for accepting return of unused medical items that limits those who may retrieve such returned items to authorized persons.

It is a further object of the present invention to provide a method for accepting return of unused medical items that correlates a returned item with a previous dispensing event related to such item.

It is a further object of the present invention to provide a method for accepting return of unused medical items that enables crediting of a patient's account for the return of an item.

It is a further object of the present invention to provide a method for accepting return of unused medical items that tracks an amount wasted of such item and the reasons therefore.

Further objects of the present invention will be made apparent in the following Best Modes for Carrying Out Invention and the appended claims.

The foregoing objects are accomplished in a preferred embodiment of the present invention by an apparatus for accepting return of unused medical items and for securely storing such items for subsequent delivery to an authorized person. In the preferred form of the present invention unused medical items include those items previously dispensed which were not used, as well as those items which were partially used and which have a remaining portion that is considered waste.

The apparatus of the present invention is used in connection with a medical dispensing system. The system includes automated dispensing devices for dispensing medical items in which the dispense of such items is controlled and tracked. The system includes a computer which has a database stored in memory. The database includes a plurality of records related to patients and the medications prescribed for such patients. The database also includes records concerning authorized users of the system. Information concerning medications and the corresponding locations from which they can be dispensed by the system are also stored in the database.

The system includes a plurality of display terminals connected to the computer in a network. The display terminals include a data input device and a data output device. Authorized users of the system are able to identify themselves to the system using the input device of the display terminals. Users are further able to select patients, dispense medications and to track the use of medications through data input and output at the display terminals.

The present invention includes an apparatus for accepting return of unused medical items that have previously been dispensed by the system. The device stores such returned items in a secure manner until instructed to deliver such items to an authorized person.

The apparatus includes a housing with a return drawer and a retrieve drawer. The return drawer and retrieve drawer are mounted adjacent to each other in the housing. The return drawer includes a pocket therein. The pocket is accessible from outside the housing when the return drawer is in an open position. The pocket is inaccessible with the return drawer in a closed position. The pocket has an opening in a lower portion thereof. A trap door is mounted adjacent to the opening. The trap door is movable between a first position where it blocks the opening, and a second position where it is disposed away from the opening. The position of the trap door is controlled by an actuator.

The retrieve drawer has a retrieve area therein. The retrieve area is accessible from outside the housing when the retrieve drawer is in a delivery position. When the retrieve drawer is in a secure position the retrieve area is not accessible from outside the housing.

The opening of the return drawer is controlled by a first latch. The first latch opens responsive to a first signal from a connected display terminal. A second latch controls the opening of the retrieve drawer. The second latch enables opening of the retrieve drawer responsive to a second signal from the display terminal.

When a user has a medical item to be returned they input identifying data through the input device at the display terminal. The input data is compared to user records stored in the database of the computer. If the data input corresponds to that of an authorized user, the user is then prompted through the output device on the display terminal through a series of steps. The steps enable identifying the information in the database concerning the medical item which is to be returned. In response to the identification of the medical item to be returned, the display terminal outputs the first signal which enables the return drawer to be opened.

The position of the trap door which bounds the pocket in the return drawer is controlled by an actuator. When the return drawer is opened the actuator moves the trap door to close the pocket. The user places the returned item in the pocket and then moves the return drawer to the closed position.

When the return drawer is closed the actuator moves the trap door to a second position. In the second position of the trap door the pocket is open to the retrieve area of the retrieve drawer. The returned item moves by the force of gravity out of the pocket and into the retrieve area. The next time an authorized user returns an item to the return drawer the pocket will be empty.

Returned items are stored in the retrieve area of the retrieve drawer until a person authorized to access the retrieve drawer inputs identifying data through the input device at the display terminal. This data is compared to user records stored in the database which contain information on users authorized to have access to the retrieve area. If the data input corresponds to information in a record in the database, the authorized user is enabled to input further data which causes the display terminal to generate the second signal opening the second latch. This enables the retrieve drawer to be opened and the returned medical items to be accessed for removal.

In the preferred embodiment, the computer is programmed to enable a user who is returning a wasted item to indicate the amount being returned and the reason why the amount is wasted. The system further enables an authorized user who is returning an item which has not been used, to credit the patient for return of the item.

BRIEF DESCRIPTION OF DRAWINGS

FIG. 8 is a side view of the trap door used in connection with the return drawer.

FIG. 9 is a front view of the trap door shown in FIG. 8.

FIG. 10 is a top plan view of the trap door shown in FIG. 8.

FIG. 12 is a user identification screen display output by a display terminal through which a user identifies himself or herself to the system.

FIG. 13 is a patient browser screen display output at the display terminal.

FIG. 14 is a patient profile screen display output at the display terminal.

FIG. 15 is a medication order screen display output at the display terminal.

FIG. 16 is a patient usage browser screen display output at the display terminal.

FIG. 17 is a return supply screen output at the display terminal.

FIG. 18 is a return amount screen output at the display terminal.

FIG. 19 is a wasted supply screen display output at the display terminal.

FIG. 20 is a retrieve inventory screen output at the display terminal.

BEST MODES FOR CARRYING OUT INVENTION

Figure 1:
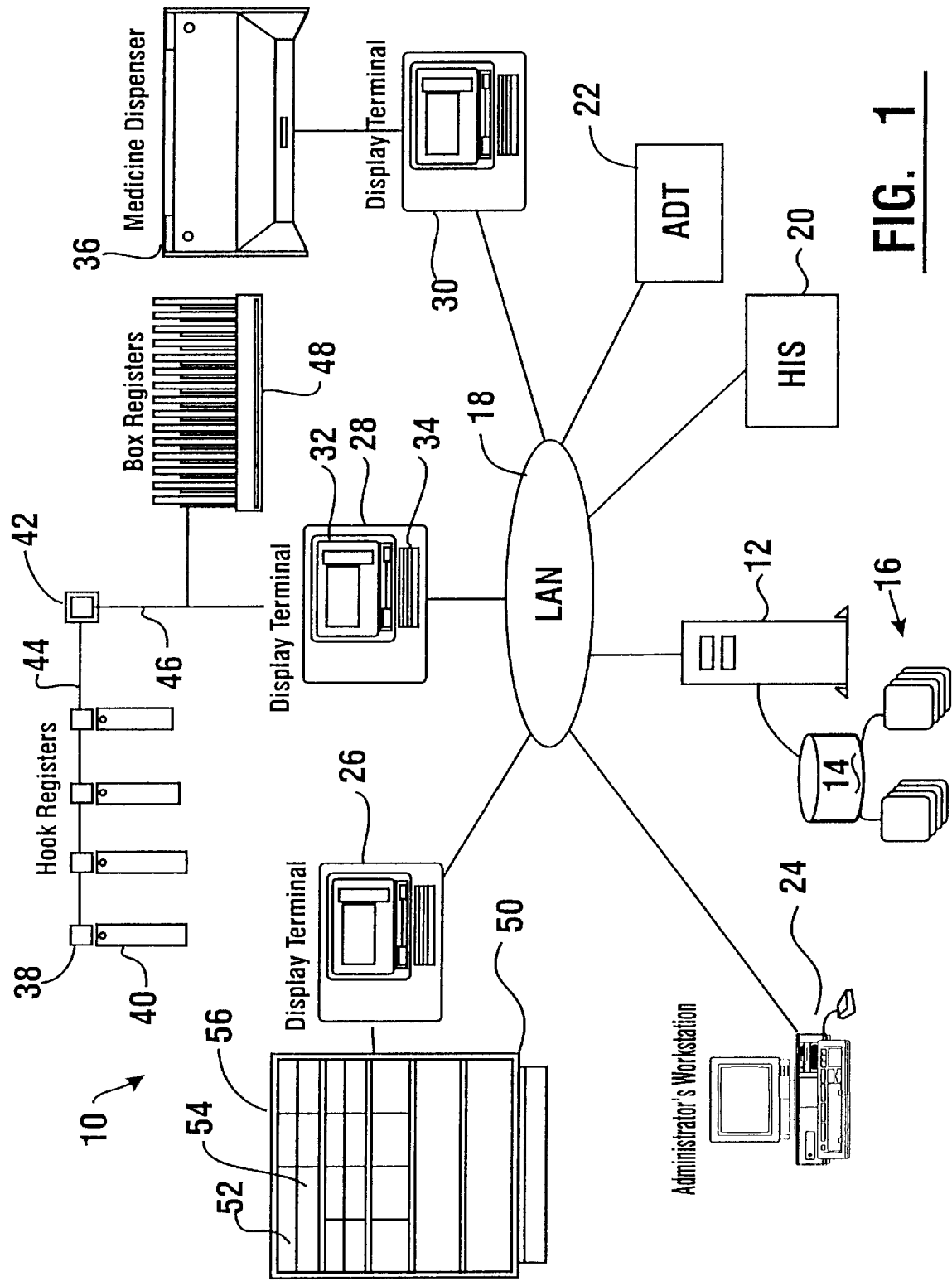
FIG. 1 is a schematic view of a system for dispensing and tracking medical items which includes the apparatus for accepting return of unused medical items of the present invention.

Referring now to the drawings and particularly to FIG. 1 there is shown therein a system for dispensing medical items generally indicated 10. The system includes a computer 12 which in the preferred form of the invention is a file server. The computer has therein in storage a database schematically indicated 14. The database includes a plurality of different types of records schematically indicated 16. Although only one computer is shown, it should be understood that embodiments of the invention may include many computers and databases.

The computer 12 communicates with other parts of the system 10 through a local area network (LAN) schematically indicated 18. In the preferred form of the invention the LAN uses the TCP/IP protocol for communication, but other network protocols may be used.

LAN 18 is in communication with other computer systems that operate within a medical facility, including a hospital information (HIS) system 20. The HIS is a separate computer network within a hospital that tracks information such as patient invoicing, medical history, and other information. LAN 18 is also connected to the hospital's admission-discharge-transfer (ADT) system 22. ADT system 22 is likewise an independent network of computers that tracks each patient during their stay in the medical facility. In the preferred form of the invention, system 10 is also connected through LAN 18 to the hospital's pharmacy system which includes information on the medications that have been prescribed for patients in the medical facility and the frequency at which such medications are to be administered. Such information can be accessed by the computer 12 through the LAN from the ADT System 22 or from a separate pharmacy system which is connected to the LAN.

System 10 further includes an administrator work station (AWS) 24. AWS 24 is preferably a computer which includes input devices such as the keyboard or mouse shown. AWS 24 further includes an output device which in the version shown is a CRT screen. AWS 24 is used to configure the system by assigning the locations for the various devices and medications stored within the system. AWS 24 is also used to program computer 12 and to set up records in the database 14. AWS 24 can also be used for tracking the use of medical items, monitoring inventory and generating orders to replenish inventory. As AWS 24 is a computer, it includes its own memory for storing various records and for carrying out programmed functions in accordance with the particular requirements of the system.

System 10 further includes a plurality of display terminals. Three display terminals 26, 28 and 30 are shown. Each display terminal preferably includes a data output device which is in the form of a screen 32. Screen 32 is preferably a touch screen which enables a user to input instructions by moving their finger on or adjacent to the screen. As a result the touch screen also serves as a data input device. Each display terminal also preferably includes a card reader 34. Card reader 34, as later explained, is used for reading encoded cards which are used by authorized users of the system to access the display terminals. The cards used in connection with the card readers are preferably magnetic stripe cards, but alternatively, optically encoded cards or so called "smart" cards, which include a programmable memory on the card, may be used.

Each display terminal includes a processor and a memory. The display terminals communicate with each other and with other components of the system through LAN 18. The display terminals also include interfaces and device drivers for controlling connected hardware devices which dispense and track medical items.

Display terminal 30 is shown in connection with a medicine dispenser 36. In the preferred form of the invention, medicine dispenser 36 is capable of dispensing to a user medical items which include oral medications such as pills and capsules. Alternatively, dispenser 36 may dispense injectable liquids or other types of medical items. It should be understood that although only one medicine dispenser 36 is shown connected to display terminal 30, in embodiments of the invention several medicine dispensers or other types of devices may be connected to a display terminal.

Display terminal 28 is shown in connection with a plurality of hook registers 38. Hook registers 38 each hold a plurality of medical items 40 which are suitable for hanging on the hook registers. Medical items 40 may be in the form of catheters, or other medical appliances or devices which must be monitored but which are generally not controlled as closely as narcotics. Hook registers 38 are connected to a hook controller 42 on a communications bus 44. The hook controller 42 polls the hook registers 38 to determine the number of items added or subtracted at each. The hook controller then passes the information to display terminal 28 through a data bus 46.

Data bus 46 is also in connection with a plurality of box registers 48. Box registers 48 hold medical items commonly placed in boxes. The box registers 48 provide an electrical signal to indicate that an item has been removed or replaced. The electrical signal is communicated on data bus 46 to the display terminal 28. The display terminal 28 operates to communicate information about the status of the items at the hook registers to the remainder of the system.

Display terminal 26 is shown in connection with a key lock drawer module 50. The lock drawer module 50 includes a plurality of drawers. Each drawer contains medical items such as medications. When an authorized user requests a particular medical item that is contained within a drawer of the key lock drawer module 50, the appropriate door opens to enable the user to access the medical item.

It should be understood that although each of the display terminals 26, 28, 30 are shown in connection with different types of devices for dispensing items, each display terminal may have a plurality of each type of device attached thereto.

The operation of system 10 to dispense medical items and to track the use of such items for patients is described in detail in co-pending U.S. patent application Ser. No. 08/361, 793 filed Dec. 16, 1994 which is owned by the assignee of the present invention. The disclosure of this pending U.S. Patent Application is incorporated into this Application by reference as if fully rewritten herein.

The lock drawer module 50 includes apparatus for accepting unused medications. Such unused medications may include medications that were dispensed for a patient from system 10 and which were not used at all. Such a medical item should be indicated as not used in the patient's record and the patient should be credited for the value of the item that was not used. Such unused item should be saved for later use.

Another category of unused items includes those items that were partially used or which should not be administered to a patient. This may occur in situations where a medical item has been dropped or contaminated or where the medical item is beyond its expiration date. Such items must be monitored and properly disposed of.

Lock drawer module 50 includes a return drawer 52 and a retrieve drawer 54. Return drawer 52 and retrieve drawer 54 are used in connection with returning unused medications. Although return drawer 52 and retrieve drawer 54 will be discussed in connection with both types of unused medical items it will be understood by those skilled in the art that it may be preferable in many embodiments to have separate return and retrieve drawers for returning unused medications of the waste and reusable varieties. Such separate return and retrieve drawers may be housed within the housing 56 of lock drawer module 50 or each may be part of a separate module. Alternatively, the return and retrieve drawers may in other embodiments be configured as stand alone devices having a separate housing.

Figure 2:
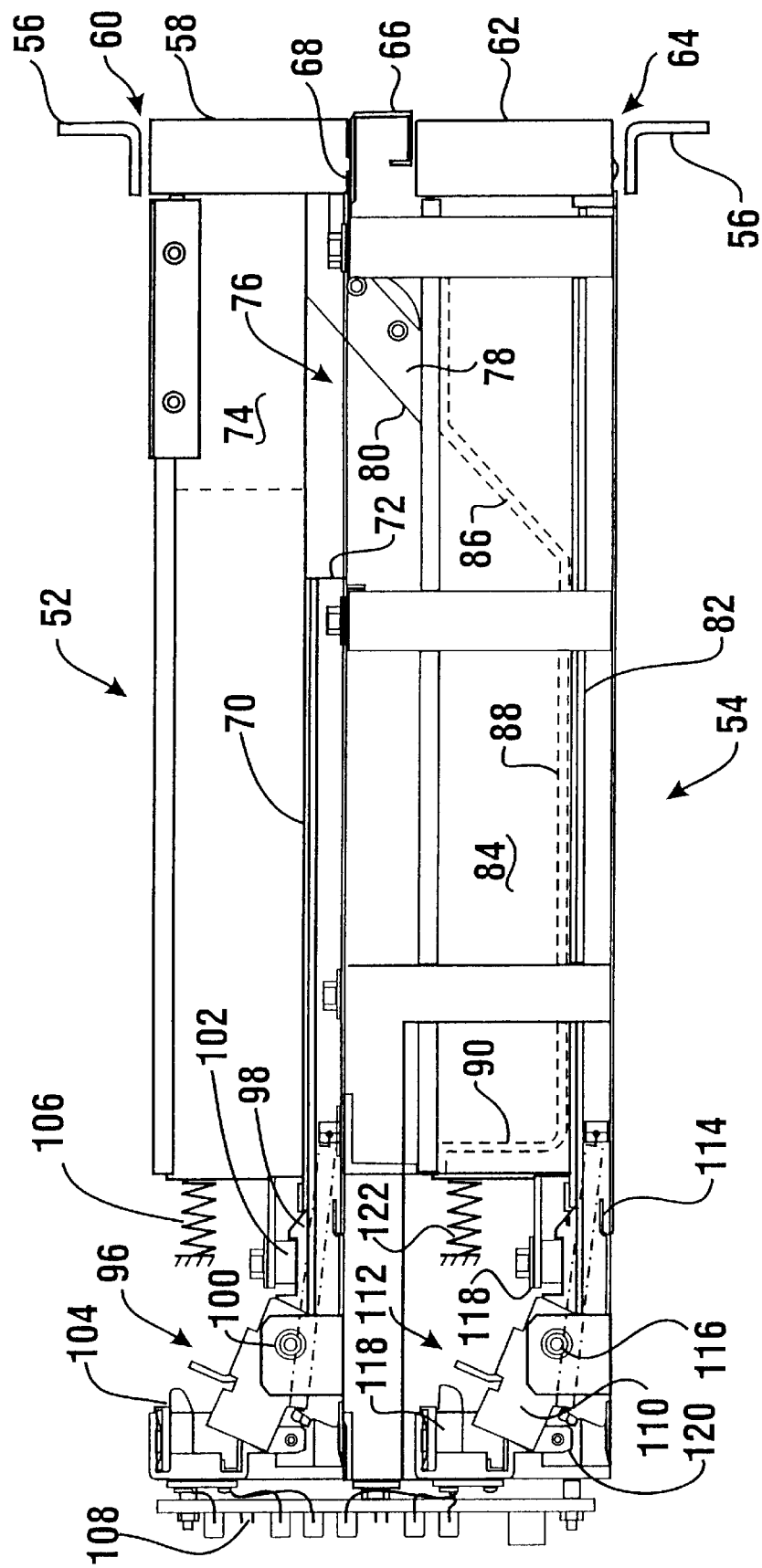
FIG. 2. is a cross sectional view of the return drawer and the retrieve drawer of the apparatus of the present invention.

Return drawer 52 and retrieve drawer 54 are shown from the side within housing 56 in FIG. 2. As shown in FIG. 2, return drawer 52 is in a closed position and retrieve drawer 54 is shown in a secure position. Return drawer 52 includes a face piece 58. Face piece 58 is positioned at the front of the return drawer and in the closed position extends in a return drawer opening 60 in the housing. Retrieve drawer 54 includes a face piece 62 at the front thereof. Face piece 62 is positioned in a retrieve drawer opening 64 in the housing when the retrieve drawer is in a secure position.

Positioned between return drawer opening 60 and retrieve drawer opening 64 is a divider 66. Divider 66 includes an inward extending shelf surface 68 which extends in an inward direction in the return drawer opening.

Figure 5:
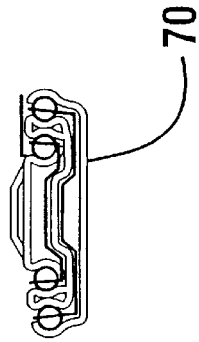
FIG. 5 is a cross sectional view of a slide used for movably supporting the preferred form of the return drawer and retrieve drawer of the present invention.
Figure 4:
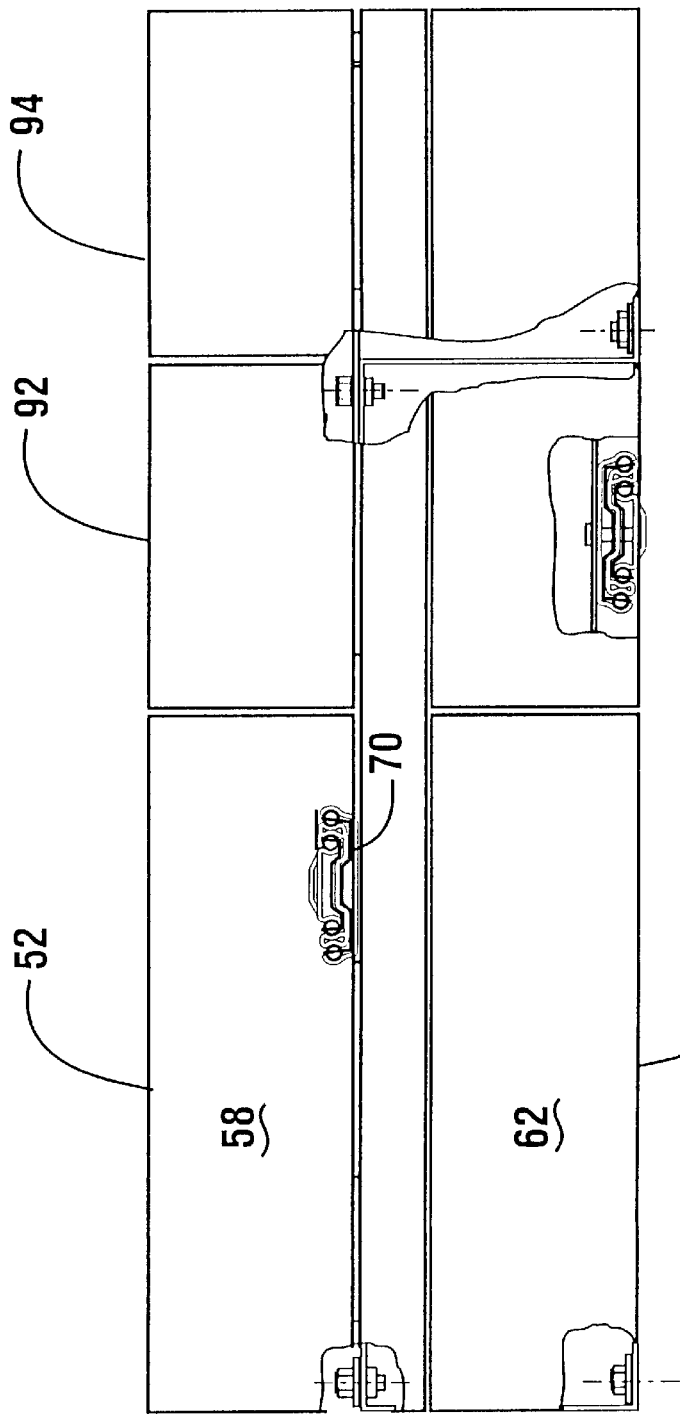
FIG. 4 is a partially sectioned front plan view of the return drawer and the retrieve drawer, as well as other drawers adjacent thereto for holding medical items to be dispensed.

Return drawer 52 is movable on a pair of telescoping slides 70. Telescoping slides 70 enable return drawer 52 to move outwardly in the return drawer opening 60 from the position shown in FIG. 2. Telescoping slides 70 are shown in greater detail in FIG. 5. Telescoping slides 70 are preferably of the ball bearing type and include a built in stop which limits the outward travel of return drawer 52 as hereinafter described. Telescoping slides 70 terminate adjacent a wall 72 when return drawer 52 is in the closed position shown in FIG. 2.

Figure 6:
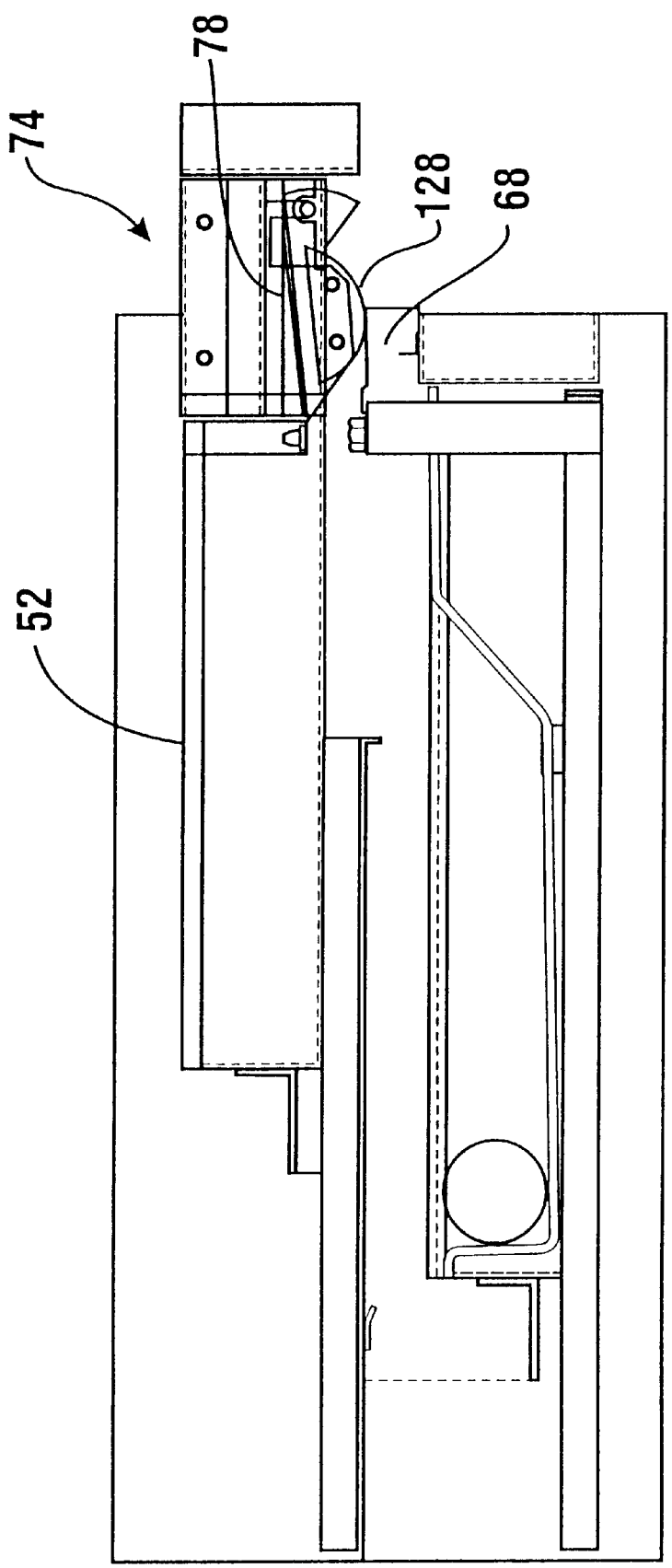
FIG. 6 is a cross sectional view with the return drawer shown in an open position.
Figure 7:
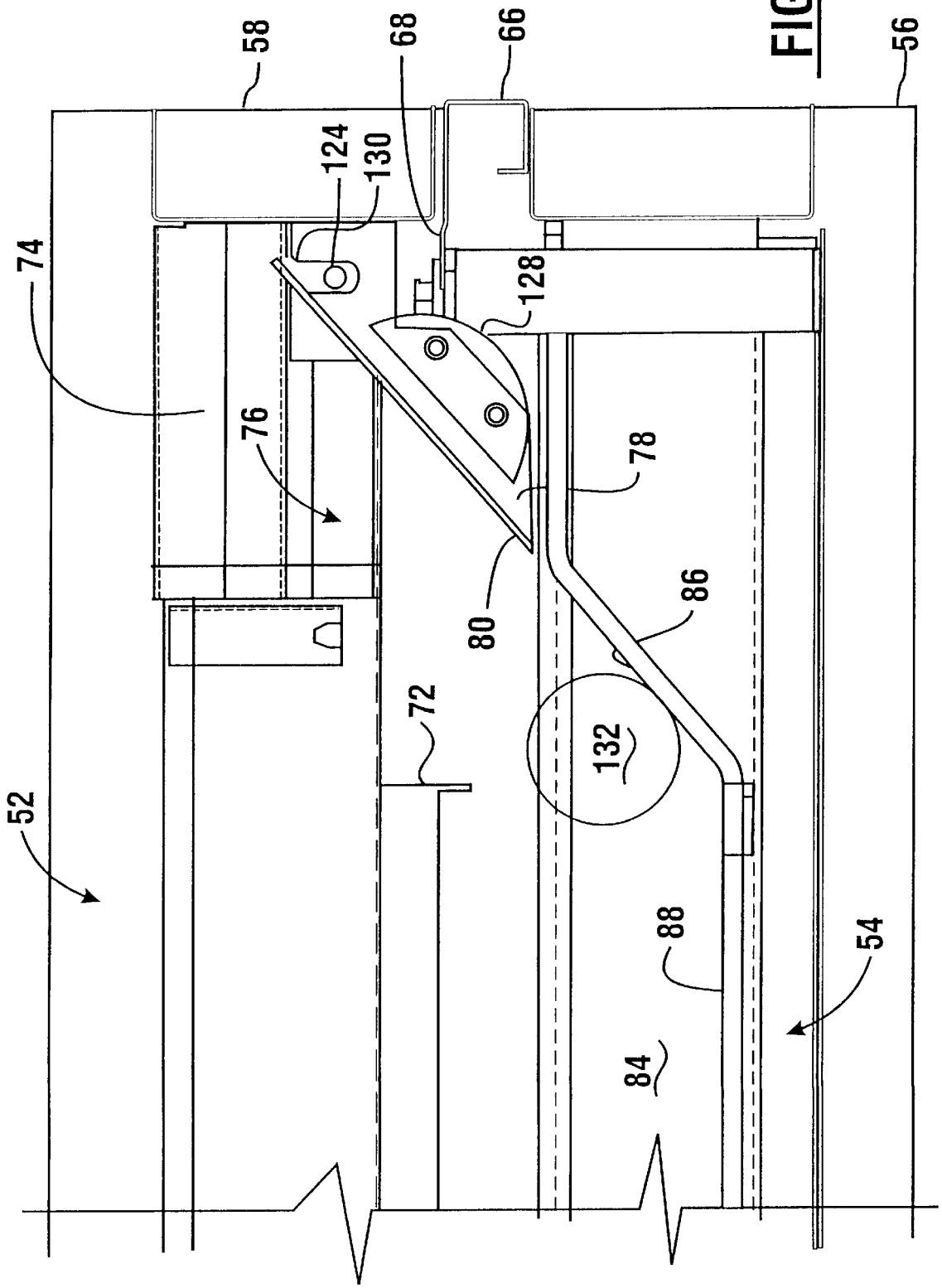
FIG. 7 is a cross sectional view showing the return drawer in a closed position and a medical item moving from the return drawer to the retrieve area of the retrieve drawer.

Return drawer 52 includes a pocket 74 therein. Pocket 74 has an opening, generally indicated 76, in its lower surface. A trap door 78 is positioned adjacent to pocket 74. Trap door 78 includes a supporting surface 80 thereon. As hereinafter described in detail, trap door 78 is movable by an actuator so that supporting surface 80 is in a first position closing the opening 76 when the return drawer is in an open position as shown in FIG. 6. When the return drawer 52 is moved to the closed position, as shown in FIGS. 2 and 7, the actuator moves trap door 78 to a second position in which supporting surface 80 is disposed away from opening 76.

Retrieve drawer 54 is supported on a pair of telescoping slides 82. Telescoping slides 82 are similar to slides 70 which movably support the return drawer. Slides 82 extend further forward than slides 70 for reasons that will hereinafter become apparent. Slides 82 enable retrieve drawer 54 to move outwardly from the housing 56 from the position shown in FIG. 2, to a delivery position.

Retrieve drawer 54 includes a retrieve area 84 therein. Retrieve area 84 is bounded by a lead surface 86. Lead surface 86 is angled, and in the secure position of the retrieve drawer, is generally aligned with supporting surface 80 when the trap door 78 is in the second position. Retrieve area 84 is further bounded by a floor surface 88. Floor surface 88 is tapered slightly downward from lead surface 86. Floor surface 88 terminates at a generally transversely extending back surface 90. Retrieve drawer 54 is selectively movable outwardly from housing 56 so that medical items stored in retrieve area 84, may be accessed by an authorized user from outside the housing. Slides 82 include stops that prevent retrieve drawer 54 from being moved outwardly beyond the delivery position.

Figure 3:
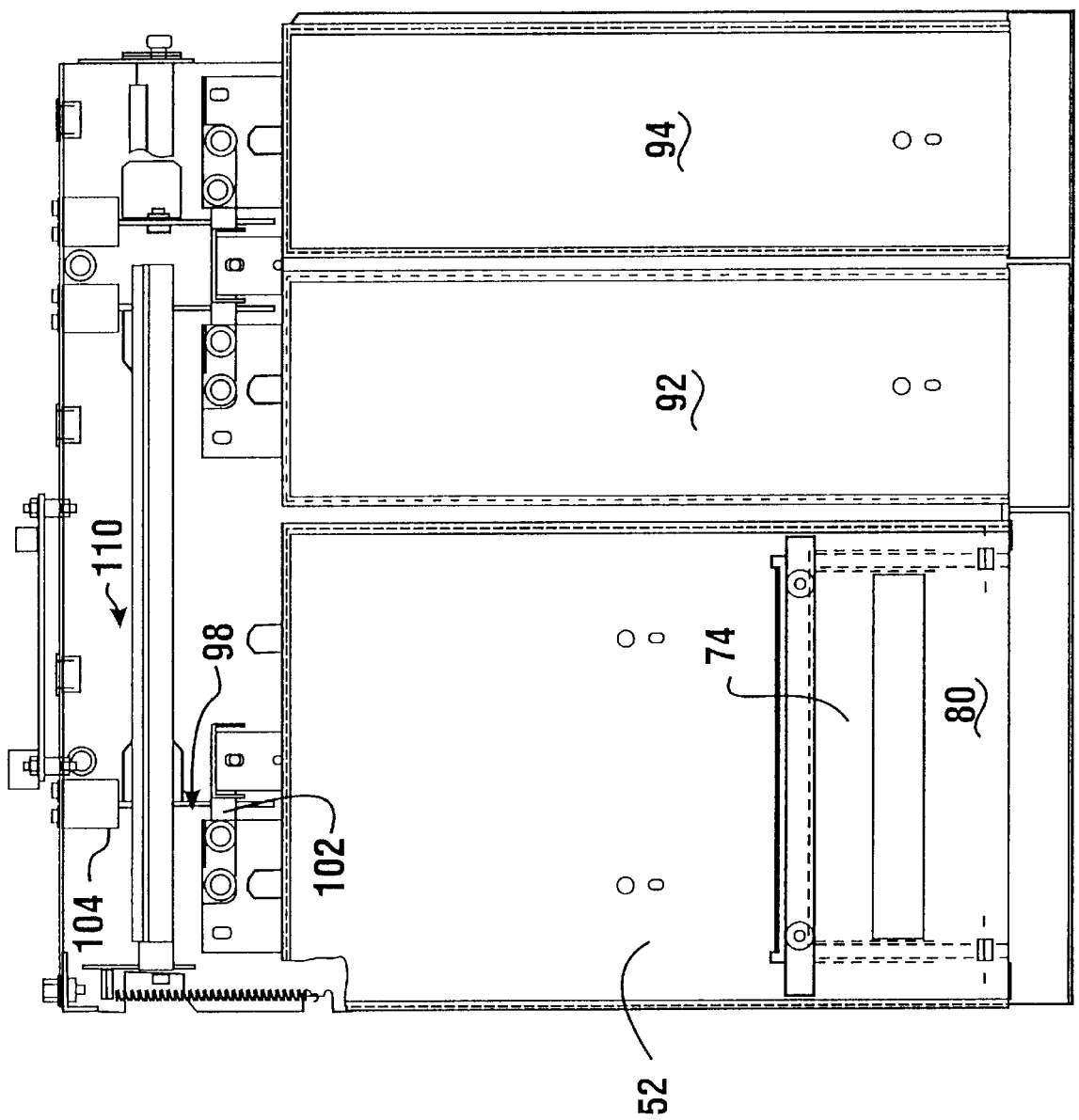
FIG. 3 is a cross sectional plan view showing the retrieve drawer adjacent other drawers for holding medical items.

As shown in FIG. 3, the return and retrieve drawers are positioned adjacent to movable medication holding drawers 92 and 94 within the housing 56. Return drawer 52 and retrieve drawer 54 are optimally sized to replace a set of standard medication holding drawers within the matrix of drawers in drawer module 50. This enables the drawer module to be configured with or without return/retrieve drawers as necessary to meet the requirements of the particular system.

As shown in FIGS. 2 and 3, return drawer 52 is connected to a first latch mechanism, generally indicated 96. Latch 96 is positioned at the rear of the drawer within housing 56. Latch 96 includes a pivotly movable lever 98 which includes a notch therein. Lever 98 is mounted for rotational movement about a pivot 100. The notch in lever 98 is sized for accepting a locking bar 102 which is attached to a tab at the rear of the return drawer. The mechanism comprising latch 96 further includes a solenoid 104. Solenoid 104 is operative responsive to a first electrical signal to move lever 98 to disengage locking bar 102. When solenoid 104 is actuated return drawer 52 is enabled to move outwardly from housing 56. A spring, schematically indicated 106, is in operative connection with return drawer 52 so that when latch 96 is disengaged, drawer 52 moves outwardly from the housing to indicate to a user that it has been opened. Spring 106 is preferably incorporated into the telescoping slides 70 which support the return drawer. Likewise, slides 70 include a stop which limits outward travel of the return drawer to that necessary to access the pocket 74. This presents access to the retrieve drawer.

Solenoid 104 includes a movable rod 108 which is pivotly connected to lever 98. Rod 108 is biased downwardly as shown in FIG. 2. When the solenoid 104 is actuated by the first electrical signal, rod 108 moves upwardly against the biasing force so as to disengage lever 98 from locking bar 102. Conversely when the first electrical signal is discontinued the biasing force on rod 108 biases the notch in lever 98 upwardly. When return drawer 52 is moved to the closed position shown in FIG. 2, the notch in lever 98 again engages the locking bar 102 to hold return drawer 52 closed. Return drawer 52 will remain closed until it is again opened responsive to the first signal.

Lock drawer module 50 further includes a mechanical locking mechanism generally indicated 110. Mechanical locking mechanism 110 enables locking and unlocking of the various drawers within the module using a key or other physical device independent of signals generated by the system. Locking mechanism 110 does not form part of the present invention and will not be further described.

Retrieve drawer 54 has attached thereto a mechanism comprising second latch 112. Second latch 112 is similar to first latch 96. It includes a lever 114 which is rotatably mounted about a pivot 116. Lever 114 includes a notch for engaging a locking bar 117 and is movable to disengage the locking bar responsive to a solenoid actuator 118. Solenoid actuator 118 includes a downwardly biased rod 120 which is pivotly attached to lever 114. Solenoid 118 is operative responsive to receipt of a second electrical signal to cause lever 114 to disengage locking bar 117. This enables the retrieve drawer to move outwardly from the housing to a delivery position. A spring 122 biases the retrieve drawer outwardly such that it automatically moves outward from the housing responsive to the second signal being delivered to solenoid 118. Stops on telescoping slides 82 limit outward travel of the retrieve drawer to the extent necessary to access the retrieve area. As is the case with the return drawer, when retrieve drawer 54 is returned to the housing the notch in lever 114 engages locking bar 117 to again hold the retrieve drawer in a secure position.

Trap door 78 is shown in greater detail in FIGS. 8–10. Trap door 78 includes a pair of pivot pins 124 that extend outwardly from each side thereof. Trap door 78 further includes a pair of spaced legs with mounting holes 126. As shown in FIG. 7, mounting holes 126 are used for fasteners which secure arcuate cams 128 to the trap door. Cams 128 are part of an actuator which moves the trap door in the manner hereinafter discussed. Trap door 78 also includes a stop surface 130. Stop surface 130 is part of a stop which limits travel of the trap door in its second open position as shown in FIG. 7.

Figure 11:
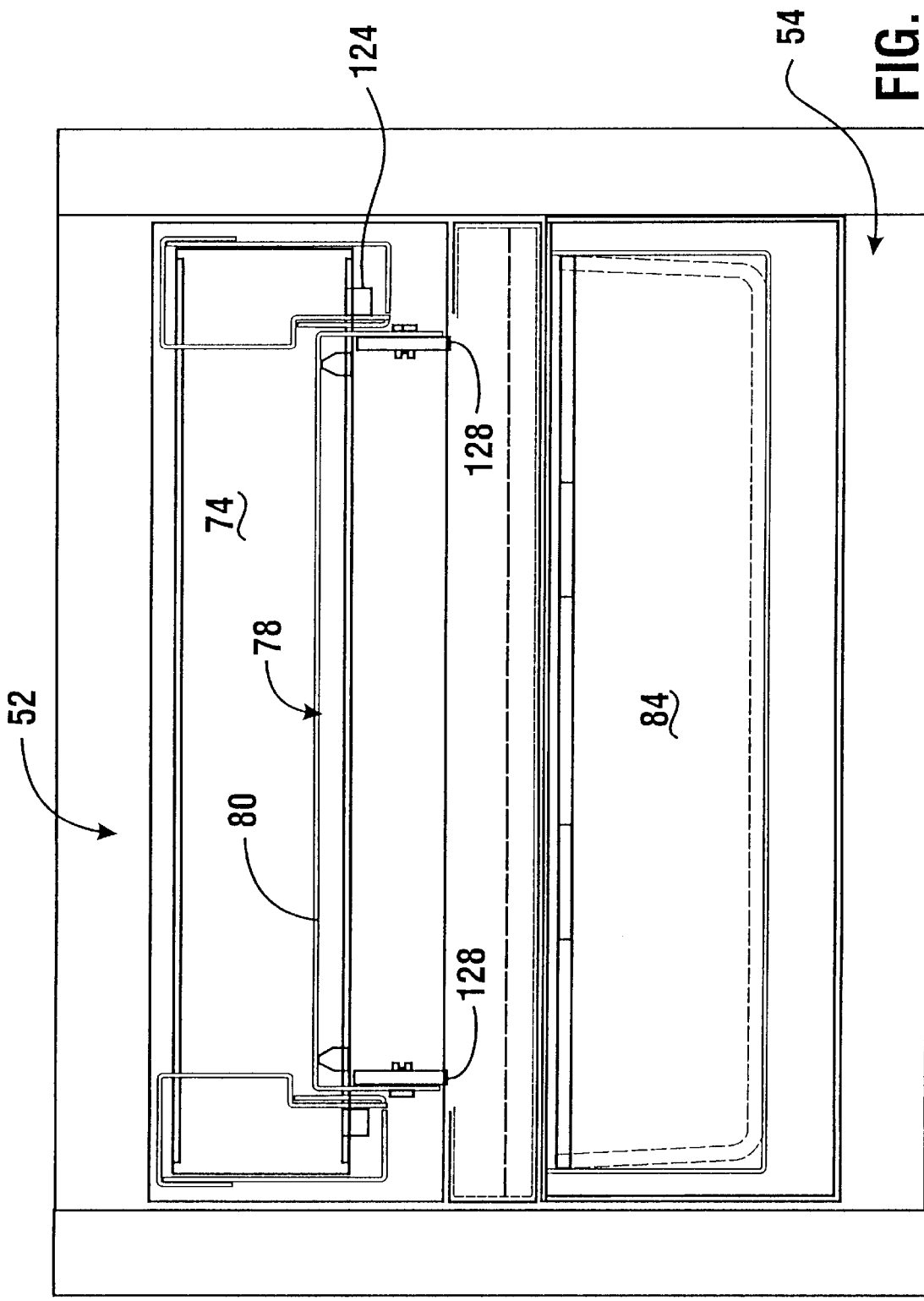
FIG. 11 is a front cross sectional view of the return drawer and the retrieve drawer.

As shown in FIG. 11, trap door 78 includes two cams 128 which are positioned in spaced apart relation adjacent to each of the pivot pins 124. Pivot pins 124 are positioned in openings in side walls which bound pocket 74 and which enable trap door 78 to rotatably move between the first and second positions.

When a medical item is to be returned, latch 96 on the return drawer is opened as the display terminal 26 delivers a first signal to solenoid 104. This causes return drawer 52 to move outwardly to the open position shown in FIG. 6. In the open position of the return drawer, pocket 74 is accessible outside the housing to a user. A user is able to deposit an unused medical item in the pocket.

As return drawer 52 moves to the open position the cams 128 on the trap door engage the inward extending shelf surface 68 of divider 66. The engagement of cams 128 with this cam engaging surface moves the trap door to the first position in which it closes the opening 76 in the pocket 74. The engagement of the cams 128 with the inward extending surface serve as parts of the actuator for moving the trap door 78 as the return drawer 52 is opened. The outward movement of return drawer 52 is limited by the stops on its supporting slides so that the trap door cannot be opened when the return drawer is in the open position.

After a user has inserted an unused medical item in pocket 74, return drawer 52 is moved inward to the closed position. In the closed position the pocket is no longer accessible from outside the housing 56. As return drawer 52 is moved inwardly the cams 128 attached to trap door 78, disengage from the surface 68. This enables trap door 78 to rotate about pivot pins 124 which comprise a pivot, to the position shown in FIG. 7. As supporting surface 80 of trap door 78 moves it makes pocket 74 accessible to retrieve area 84 of the retrieve drawer through opening 76. The returned unused medical item, which is represented by vial 132 in FIG. 7, is enabled to pass from the pocket 74 into retrieve area 84.

The rotation of trap door 78 is limited by the engagement of stop surface 130 with an inside surface of face piece 58 of the return drawer, which together comprise a stop which limits movement of the trap door. The stop is disposed on an opposite side of the pivot for the trap door from the cams. As a result the engagement of the cams with the cam engaging surface as the return drawer is opened moves the trap door to disengage the stop.

In the second position of trap door 78, supporting surface 80 is aligned with lead surface 86 bounding retrieve area 84. As a result the medical items deposited in pocket 74 are enabled to pass downwardly by the force of gravity into the retrieve area 84. Upon reaching the retrieve area the medical item moves on the slanted floor surface 88 to the rear of the retrieve area 84 until it engages the back surface 90 or a previously deposited medical item. It will be understood by those skilled in the art that although vial 132 is shown as the returned item in FIGS. 6 and 7, the present invention may also be used with other types of returned medical items.

Once the medical item has passed from the pocket 74 into the retrieve area 84 in the retrieve drawer 54, the return drawer is ready to accept the return of further unused medical items. The next time that the return drawer 52 is opened responsive to the first electrical signal, the pocket 74 will again be empty.

The construction of the return and retrieve drawers is specifically designed to prevent persons who place medical items in the return drawer from accessing items that are stored in the retrieve area of the retrieve drawer. This is done by the construction which holds the return drawer in its opening 60 in the open position and which holds the trap door closed when the return drawer is open.

When an authorized person wishes to remove the items from the retrieve drawer, second latch 112 is opened responsive to the second electrical signal to solenoid 118. In response to the unlatching of the second latch, the retrieve door 54 moves to a delivery position in which the retrieve area 84 is accessible from outside the housing 56. The authorized user is then permitted to review and inventory the returned medical items and remove them for proper disposal or re-use. It should be noted that the trap door 78 is configured so that the retrieve drawer 54 may be opened to provide access to the medical items stored in the retrieve area in a delivery position even though the trap door is in the open, second position. Upon the removal of the returned medical items by the authorized user, the retrieve drawer 54 is closed and will be held in a secure position by second latch 112.

The operation of the return and retrieve drawers within the system 10 is now explained with reference to FIGS. 12–17. A user seeking to return an unused medical item approaches the display terminal 26 that is in connection with the electronic drawer module 50 which contains the return and retrieve drawers. The user is presented on the touch screen of the display terminal with a log on ID screen 134 shown in FIG. 12. The user inputs their user ID through the touch screen by placing a finger adjacent each of the numbers in the ID screen representative of their user ID number. The user then places a finger adjacent the "enter" button when they have entered their number. Alternatively the user may swipe a card through the card reader 34 on the display terminal to enter their identification number. In some embodiments of the system a user will be required to swipe their card and enter a different personal identification number to identify themself to the system.

After a user has input their identifying data through the input device of the display terminal, the computer 12 compares the data input to at least one authorized user record in the database 14. The user records preferably contain information concerning the card numbers, identification numbers and/or personal identification numbers which correspond to users authorized to dispense medications and/or to place unused medications in return drawer 52. Computer 12 preferably checks the user records for a record including information corresponding or having a predetermined programmed relationship to the data input by the user at the display terminal. If an appropriate correlation is found, the computer then authorizes the display terminal to provide further system access to the user who can go forward with further process steps.

Figures 12, 13:
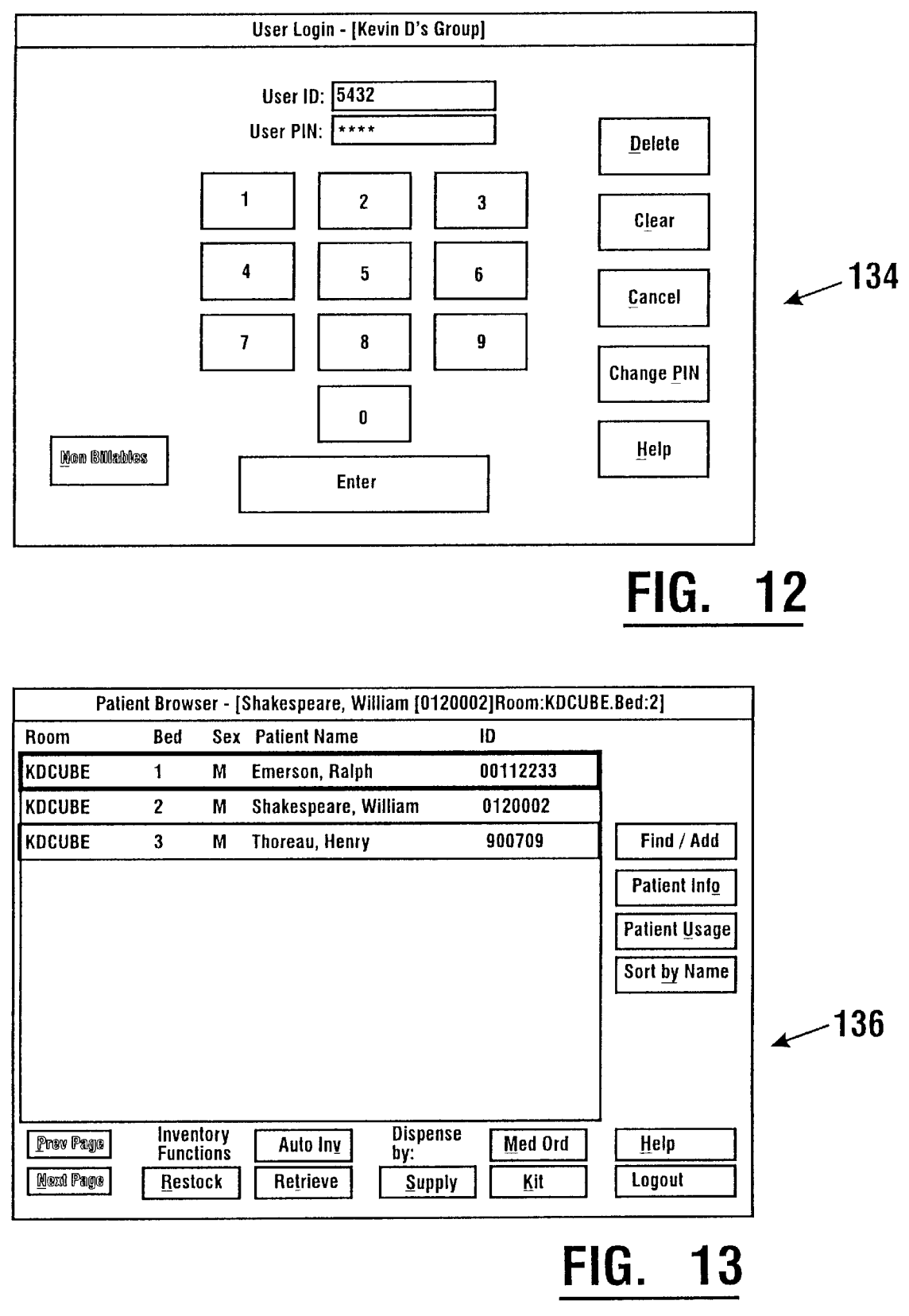

After a successful log in by an authorized user, the display terminal in the preferred embodiment displays a patient browser screen 136 shown in FIG. 13. The patient browser screen 136 enables the user to scroll through a list of patients whose medications can be returned at the return drawer 52 in the drawer module 50. Scrolling through the list of patients is done by touching the "page buttons" on the patient browser screen.

The user may select a particular patient by touching the screen adjacent to the patient name. This causes the patient's name to be highlighted on the patient browser screen as shown in FIG. 13. If the user is taking medications from accessible areas, such as hook registers or box registers, the user may now take such items from their storage locations. This will cause the items taken to be automatically charged to that particular patient's account and recorded in the patient usage information stored in the database related to that patient. If a user is only taking accessible items they may touch the "log out button" which returns the display terminal to the log on screen. However if the user is desiring to return an unused medication the user highlights the "patient info button" on the touch screen.

Highlighting the "patient info button" on the patient browser screen 136 causes the display terminal to display a patient profile screen indicated 138 in FIG. 14. The patient profile screen 138 shows information about the patient. However, if the user wishes to return a medication they use the touch screen to highlight the "close" box on the patient profile screen. This returns the display terminal to the patient browser screen 136. If the user wishes to review medication orders for the particular patient, and possibly dispense an item, they would touch the "med ord button". This causes the medication order screen, generally indicated 140 in FIG. 15, to appear on the screen of the display terminal.

The medication order screen includes a listing of the medications prescribed for the particular patient. If the user needed to dispense a medication for the particular patient they could highlight the medication to be dispensed and then touch the "dispense button". This will cause the appropriate medication dispenser to dispense the medication or a drawer in the lock drawer module 50 containing the medication to open. If the medication requested is a controlled substance, such as a narcotic, the computer is preferably programmed to require a second authorized user to witness the dispense. In this case before hitting the "dispense button", the system will require a second user to log on and will generate the second log on screen 134. Once the second user has logged on then actuating the "dispense button" on the medication order screen will cause the medication to be dispensed. The user may return to the patient browser screen 136 by touching the "close" button.

The computer stores information about each dispense event for the patient in its database. Such information is stored in dose records and other records which correspond with the patient, the user and the witness user. It should be noted that the patient browser screen includes "buttons" for dispensing kits and supplies as well as dispensing by med orders. As a result if a particular procedure or treatment requires a number of items, information on these items is stored as a "kit" in the database. The user can display a list of kits by touching the "kit button" and can dispense all items in a kit through a single dispense request at the display terminal. Likewise, a user can obtain a list of available supplies by touching the "supply button". The user may then dispense a supply selected from the list.

If the user is returning an unused medication, the user touches the "patient usage button" on the patient browser screen 136. This causes a patient usage browser form, generally indicated 142 in FIG. 16, to be displayed at the display terminal. The patient usage browser form shows the status of the various medications that have been previously dispensed for the patient based on the dose records in the database. If a medication is to be returned, the user touches the screen to highlight the "taken" medication that is to be indicated as returned. This input corresponds with the dose record data in the database and indicates to the system the item being returned. In this example a returned medication is one which is good and which may be later administered to another patient.

Some returned items that are suitable for use by another patient may be returned to their original storage location. These are generally medical items such as devices or medications which are not controlled substances. If the item being returned is one which the programming of the system allows to be returned to its original location for immediate reuse, highlighting the "return button" in connection with the item will cause the system to generate a screen which asks the user if they will return the item to its original location. For some large items the system may be programmed to require the returned item to go back to its original location. The user can indicate through touching a button on the optional screen display that they are returning the item to its original location. This may cause a medication dispensing drawer to open or a location to be otherwise made accessible for the user to place the item in the dispensing location.

For some items the user may have the option to return the item to an original dispensing location or into the return drawer 52. The user may select the return drawer in response to an optional screen. In many cases, and particularly if the item to be returned is a controlled substance, the programming of the system will require the item to be placed in the return drawer. In these situations the user touches the "return button" on the patient browser screen 142 and no other return option screens are presented.

In response to touching the "return button" on the patient usage browser screen 142, for items being returned to a return drawer, the display terminal generates a return supply screen 146 shown in FIG. 17. Screen 146 shows a list of available return drawers similar to return drawer 52. Multiple return drawers may be used for different types or sizes of return medications. Alternatively, different return drawers may be used to segregate returned items for which quality will need to be rechecked from those items which will not need processing before being returned to available inventory. When more than one return drawer is available the display terminal generates a different first signal to selectively open each return drawer. Alternatively if there is only one return drawer connected to the display terminal, return supply screen 146 can be eliminated.

The user highlights the desired return drawer on the return supply screen 146 where the medication will be returned.

The user then touches the "select button". This causes the display terminal to display the return amount screen 148 shown in FIG. 18. The user preferably indicates the reason for the return in the "return reasons" box on screen 148. This is done by scrolling through a list of reasons and touching the appropriate one. This information is stored in correlated relation with the fact and amount of the return in the database.

The user is also required to input a "return amount" through the key pad displayed on the screen. This will generally be equal to the amount originally dispensed but in some cases may be less. This depends on what type of medical item is involved. For example the original dispense may have included a dose which was delivered in two vials, one of which is being returned. If the user makes a mistake inputting the reason for return or return amount they may make corrections using the "delete" and "clear" buttons on the return amount screen. The amount returned is also stored with the other information in the database.

When the user has indicated the reason and amount of the return he touches the "accept button" on the return amount screen 148. Touching the "accept button" on the touch screen causes a first signal to be generated which unlatches the first latch 96 of the appropriate return drawer 52. This causes the selected return drawer to open. The user then deposits the returned medication into the pocket 74 of the open return drawer and moves the return drawer to the closed position. Upon closing the return drawer the returned medication moves out of the return drawer and is stored in the retrieve area 84 of the retrieve drawer 54. The patient dose record is also updated to indicate that the item has been returned.

If the medication to be returned is a narcotic, the computer 12 is preferably programmed to require a witness to verify the return. If the computer is programmed in this manner for the particular medical item being returned, the log on screen will appear for the second user who is witnessing the return before return amount screen 148 appears. Once the second user who will witness the return has input their identifying information, the computer verifies that the second user is authorized to witness the return by checking the user records in the database. The system also makes sure that the witness is a different person than the user who requested the return. If the data input corresponds with a second authorized user, the display terminal returns to the return amount screen 148. After input of appropriate data as previously described touching the "accept button" generates the first signal to open the return drawer.

If the returned medical item is wasted, the user after reaching the patient usage browser screen 142 highlights the medication dose to be wasted and touches the "waste" button on the screen 142. This causes the display terminal to display the wasted supply screen 144 shown in FIG. 19. The user then touches the screen to highlight and thereby indicate the reason that the supply is being wasted. This is done by scrolling through a list of reasons. The user also enters the amount of the original dose dispensed that is wasted.

In response to the user entering the reason and amount of the medication to be wasted, and touching the "accept button" on the waste supply screen 144 the first signal is generated by the display terminal. The return drawer 52 opens to accept the medication. In most systems the return drawer for wasted medications will be a separate return drawer from those used for accepting reusable medications. The user then deposits the wasted medication in the return drawer and closes it, this causes the wasted medication to be stored in the retrieve area of the associated retrieve drawer.

In response to a user inputting data indicating the reason and amount in the wasted supply screen, the computer operates to correlate the data input with the dose record for the dose previously delivered. The computer then stores the information about the amount and reason the medication was wasted in the database. This information is stored in the dose records which information corresponds with the user and the patient.

When the medical item to be wasted is a controlled substance, such as a narcotic, the system is preferably programmed so that a second authorized user is required to witness the wasting of the unused portion of the medication. When this occurs the computer 12 is programmed to include a flag with the medical item in the database which requires a witness to any waste event. When a user requests to waste such a flagged medical item in the patient usage browser screen 142, a log on screen 134 appears at the display terminal so that a second user can log on to witness the waste of the unused medical item. After the second user has logged on and the data input is correlated with a user record for a second, different authorized user, the waste supply screen 144 is generated. After input of the reason and amount data, and touching the "accept button" the return drawer for the waste medication will open. The user will place the wasted medical item in the pocket thereof. Upon closing the return drawer the medication is transferred to the retrieve drawer. The identity of the witness is also stored in correlated relation with the other information concerning the wasted medication in the database.

Returned medical items are retrieved by a user who is authorized to obtain such items from the retrieve drawer 54. Such an authorized user will generally inventory them and compare them against the information contained in the database records. The user authorized to retrieve medications from the retrieve door will then dispose of them or cause them to be redistributed for dispense in the appropriate manner.

Users who are authorized to access the retrieve drawer have user records stored in database 14 which include information that they are authorized such access. Such a user logs on to the display terminal by inputting identification data on a card through the card reader, or personal identification data through the touch screen, or both. The computer then compares this information to the authorized user records stored in the database 14. An authorized user permitted to remove items from the retrieve area will input data that corresponds to a limited group user records.

The patient browser screen 136 includes a "retrieve button". The computer will respond to data input by an authorized user touching the "retrieve button" to display the retrieve inventory screen 150 shown in FIG. 20 on the display terminal. The retrieve inventory screen 150 includes a listing of all items indicated as returned in a manner which would result in their being stored in the retrieve drawer. If there are several retrieve drawers connected to a display terminal, the system may be programmed to include a screen which enables a user to select each retrieve drawer to be opened and to review the data concerning the content of each such drawer individually.

When an authorized user touches the "retrieve button" on the patient browser screen 136 the display terminal generates the second signal which causes the second latch 112 to open the retrieve drawer 54. The authorized user may then remove the medical items stored in the retrieve area. The computer also operates to update the user's records in the database to indicate that this user accessed the retrieve area of the particular retrieve drawer at the particular date and time, along with the medications indicated in the database as being in the retrieve drawer when accessed.

In the preferred form of the invention the system is programmed so the user accessing the retrieve drawer may selectively indicate which medications are being removed from a retrieve drawer. If all medications are being removed, the user touches the "empty all button" on the retrieve inventory screen 150. This will cause the computer to change its database records to indicate that the user now has custody of these items and that they are no longer in the particular retrieve drawer.

A user may alternatively indicate that they are removing only some of the items in the retrieve drawer. This is done by highlighting the particular item to be removed by touching it on screen 150. The user then indicates that this particular item has been removed by touching the "empty button". This indicates to the system that the user has taken the highlighted item and the records in the database are modified accordingly. The user after removing the indicated items closes the retrieve drawer.

If a user removing items from a retrieve drawer finds a discrepancy between what is indicated on the screen as being in the retrieve drawer, and what is actually in the drawer, a record is made in the system. This is done by the user highlighting the item concerning which the discrepancy exists and then touching the "discrepancy button" on screen 150. This causes the display terminal to display a further screen through which the user may indicate the nature of the discrepancy. The system records information concerning discrepancies so that suspicious situations may be identified. Patterns involving discrepancies associated with particular items or individuals may also be studied by review of the discrepancy information stored in the database.

As previously described with respect to users placing materials in the return drawer, a user wishing to access the retrieve drawer may first require a second authorized user with authority to access the retrieve drawer to input identifying data at the display terminal. This is preferably done by requiring a second user to log on before the display terminal displays the retrieve inventory screen 150. This will help to assure that removal of items from the retrieve drawer will be witnessed and a record of the witness will be maintained in the database. Of course other accessing schemes may be provided depending on the level of security and procedures to be used at the particular medical institution which operates the system.

In some embodiments, the retrieve drawer may also be accessed through the use of the mechanical locking mechanism 110 which may be desirable in systems where servicers prefer to rely on physical control rather than electronic control. In such cases the solenoid associated with the second latch may be disabled and one or more keys required to open the retrieve drawer. Alternatively locking mechanism 110 may require both a key and the generation of the second electrical signal from the display terminal to access the retrieve drawer.

Thus the new apparatus for accepting return of unused medical items and method of the present invention achieve the above stated objectives, eliminate difficulties encountered in the use of prior devices and systems, solve problems and attain the desirable results described herein.

In the foregoing description certain terms have been used for brevity, clarity and understanding. However no unnecessary limitations are to be implied therefrom because such terms are used for descriptive purposes and are intended to be broadly construed. Moreover the descriptions and illustrations given herein are by way of examples and the invention is not limited to the details shown or described.

In the following claims any feature described as a means for performing a function shall be construed as encompassing any means capable of performing the recited function, and shall not be limited to the particular means discussed in the foregoing description as performing that function or mere equivalents thereof.

Having described the features, discoveries and principles of the invention, the manner in which it is constructed and operated and the advantages and useful results attained; the new and useful structures, devices, elements, arrangements, parts, combinations, systems, equipment, operations, methods and relationships are set forth in the appended claims.

We claim:

1. Apparatus for accepting return of unused medical items and for storing and delivering the returned medical items comprising:

a housing;

a return drawer movably mounted in supporting connection with the housing, the return drawer having a pocket therein, the pocket having an opening, and wherein the return drawer is movable between an open position wherein the pocket is accessible from outside the housing, and a closed position wherein the pocket is within the housing;

a retrieve drawer movably mounted in supporting connection with the housing, the retrieve drawer including a retrieve area therein, wherein the retrieve area of the retrieve drawer is bounded by a lead surface, and wherein the retrieve drawer is movable between a secure position wherein the retrieve area is within the housing, and a delivery position wherein the retrieve area is accessible from outside the housing;

a trap door adjacent the opening of the pocket of the return drawer, wherein the trap door includes a supporting surface, wherein said trap door is movable between a first position wherein the supporting surface closes the opening and a second position wherein the trap door enables access through the opening;

an actuator in operative connection with the trap door, wherein the actuator is operative to position the trap door in the first position when the return drawer is in the open position and to position the trap door in the second position when the return drawer is in the closed position, wherein in the second position the lead surface is generally aligned with the supporting surface.

2. The apparatus according to claim 1 wherein said housing comprises a retrieve drawer opening, wherein said retrieve drawer is movable in said retrieve drawer opening between the secure position and the delivery position, and wherein in the secure position of said retrieve drawer said lead surface extends in a direction that is both away from said pocket and away from said retrieve drawer opening.

3. A method for accepting unused medical items and for storing and delivering such unused items, said method performed with an apparatus including a terminal including a data input device, a housing including a return drawer and a retrieve drawer, a first latch in operative connection with the return drawer and the terminal, wherein the return drawer includes a pocket therein, and wherein the pocket has an opening with a trap door selectively movable into a first position in adjacent blocking relation with the opening, and a second open position disposed from the opening, and wherein the retrieve drawer includes a retrieve area therein, said method comprising the steps of:

entering predetermined data through the data input device of the terminal;

unlatching the first latch responsive to input of the predetermined data, wherein the return drawer is rendered movable relative to the housing responsive to input of the predetermined data;

moving the return drawer outward relative to the housing to an open position, wherein the pocket is accessible from outside the housing and wherein in the open position the trap door blocks the opening of the pocket;

placing a medical item in the pocket of the return drawer when the return drawer is in the open position;

moving the return drawer to a closed position wherein the pocket is within the housing; and opening said trap door wherein the item passes from the pocket into the retrieve area of the retrieve drawer.

4. The method according to claim 3 and further comprising the step of moving said retrieve drawer to a delivery position, wherein said medical item in said retrieve area is accessible from outside said housing.

5. The method according to claim 3 wherein the terminal is in operative connection with a database and prior to entering the predetermined data, further comprising the step of creating a dose record in the database wherein the dose record includes information corresponding to a medical item previously provided, and further comprising after the data entering step, comparing the data entered to the information in the dose record for a second predetermined relationship, wherein the unlatching step is performed responsive to the data entered and the information in the dose record having the second predetermined relationship.

6. The method according to claim 5 wherein the terminal is in operative connection with the database and prior to entering the predetermined data, further comprising the step of creating a user record in the database wherein the user record includes information corresponding to an authorized user, and further comprising after the data entering step, comparing the data entered to the information in the user record for a first predetermined relationship, wherein the unlatching step is performed responsive to the entered data having the first predetermined relationship with the data in the user record and the second predetermined relationship with the information in the dose record.

7. The method according to claim 5 and prior to the unlatching step further comprising the step of inputting waste amount data through the data input device, wherein the unlatching step is performed responsive to the second predetermined relationship and the input of the waste amount data.

8. The method according to claim 3 wherein the terminal is in operative connection with a database and prior to entering the predetermined data, further comprising the step of creating a user record in the database, wherein the user record includes information corresponding to an authorized user, and further comprising after the data entering step, comparing the data entered to the information in the user record for a first predetermined relationship, wherein the unlatching step is performed responsive to the data entered and the information in the user record having the first predetermined relationship.

9. The method according to claim 8 wherein the creating step comprises creating a plurality of user records in the database, each user record including information corresponding to an authorized user, and prior to the unlatching step further comprising the steps of a second user entering second data through the data input device, and comparing the second data to the information in the user records in the database for a second predetermined relationship with the stored information in the user records, wherein the unlatching step is performed responsive to the first predetermined relationship and the second data having the second predetermined relationship.

10. A method for accepting unused medical items and for storing and delivering such unused items said method performed with an apparatus including a terminal having a data input device, a housing including a return drawer and a retrieve drawer, a first latch in operative connection with the return drawer and the terminal, and a second latch in operative connection with the retrieve drawer and the terminal, wherein the return drawer includes a pocket therein, and wherein the pocket has an opening with a trap door selectively movable into a first position in adjacent blocking relation with the opening, and a second open position disposed from the opening, and wherein the retrieve drawer includes a retrieve area therein, said method comprising the steps of:

moving the return drawer outward relative to the housing to an open position, wherein the pocket is accessible from outside the housing and wherein in the open position the trap door blocks the opening of the pocket;

placing a medical item in the pocket of the return drawer when the return drawer is in the open position;

moving the return drawer to a closed position wherein the pocket is within the housing;

opening the trap door, wherein the item passes from the pocket into the retrieve area of the retrieve drawer;

entering predetermined data through the data input device of the terminal; unlatching the second latch responsive to input of the predetermined data, wherein the retrieve drawer is rendered movable relative to the housing responsive to input of the predetermined data; and moving the retrieve drawer relative to the housing to a delivery position, wherein the item in the retrieve area is accessible from outside the housing.

11. The method according to claim 10 wherein the terminal is in operative connection with a database, and prior to the step of entering the predetermined data, further comprising the step of creating a user record in the database, wherein the user record includes user information corresponding to an authorized user, and further comprising after the data entering step, the step of comparing the data entered to the information in the user record to determine if the data has a corresponding relationship with the information in the user record, wherein the unlatching step is performed responsive to the corresponding relationship.

12. A method comprising the steps of:

(a) entering input data through a data input device;

(b) comparing the input data and stored data stored in a data store, for a predetermined relationship;

(c) unlatching a first latch responsive to the input data and the stored data compared in step (b) having the predetermined relationship, wherein the first latch is in operative connection with a return drawer movably mounted in supporting connection with a housing, and wherein the return drawer is rendered movable relative to the housing responsive to unlatching the first latch;

(d) moving the return drawer outward relative to the housing to an open position, wherein a pocket in the return drawer becomes accessible from outside the housing and wherein in the open position a trap door blocks an opening of the pocket;

(e) placing a medical item in the pocket of the return drawer when the return drawer is in the open position;

(f) moving the return drawer relative to the housing to a closed position, wherein in the closed position the pocket is within the housing;

(g) moving the trap door relative to the opening with an actuator such that when the return drawer is in the closed position the medical item is passed from the pocket through the opening to a retrieve area disposed in the housing from the return drawer.

13. The method recited in claim 12 and further comprising the steps of:

(h) entering further input data through the data input device;

(i) comparing the further input data and stored data stored in a data store, for a predetermined relationship;

(j) unlatching a second latch responsive to the further input data and the stored data compared in step (i) having the predetermined relationship, wherein the second latch is in operative connection with a retrieve drawer movably mounted in supporting connection with the housing, wherein the retrieve drawer includes the retrieve area, and wherein the retrieve drawer is rendered movable relative to the housing responsive to unlatching the second latch;

(k) moving the retrieve drawer relative to the housing wherein the medical item in the retrieve area becomes accessible from outside the housing.

14. Apparatus for accepting return of unused medical items and for storing and delivering the returned medical items, comprising:

a housing;

a return drawer movably mounted in supporting connection with the housing, the return drawer having a pocket therein, the pocket having an opening, and wherein the return drawer is movable between an open position wherein the pocket is accessible from outside the housing, and a closed position wherein the pocket is within the housing;

a first latch in operative connection with the return drawer, wherein the first latch is selectively operative to hold the return drawer in a closed position;

a retrieve drawer movably mounted in supporting connection with the housing, the retrieve drawer including a retrieve area therein, wherein the retrieve drawer is movable between a secure position wherein the retrieve area is within the housing, and a delivery position wherein the retrieve area is accessible from outside the housing;

a second latch in operative connection with the retrieve drawer, wherein the second latch is selectively operative to hold the retrieve drawer in the secure position;

a door adjacent the opening of the pocket of the return drawer, wherein the door is movable between a first position wherein the door closes the opening and a second position wherein the pocket is accessible through the opening; and an actuator in operative connection with the door, wherein the actuator is operative to position the door in the first position when the return drawer is in the open position and to position the door in the second position when the return drawer is in the closed position, wherein in the closed position of the return drawer and the door in the second position the retrieve area is in communication with the pocket through the opening;

a computer in operative connection with the first latch;

an input device in operative connection with the computer;

a data store in operative connection with the computer, wherein the data store includes data corresponding to at least one user input authorizing a user to place a medical item in the apparatus;

a medical item;

wherein responsive to a first user input through the input device the computer is operative to cause to be determined if the data store includes data corresponding to the first user input, and the computer is operative responsive to the determination that the data store includes such corresponding data to cause the first latch to cease holding the return drawer in the closed position, wherein when the return drawer is moved to the open position the medical item is enabled to be placed in the pocket, and when the return drawer is moved to the closed position the medical item passes to the retrieve area.

15. The apparatus according to claim 14, wherein the computer is in operative connection with the second latch, and wherein the data store further includes data corresponding to at least one user input authorizing a user to retrieve medical items from the retrieve area, wherein responsive to a second user input to the input device the computer is operative to cause to be determined if the data store includes data corresponding to the second user input, and the computer is operative responsive to the determination that the data store includes data corresponding to the second user input to cause the second latch to cease holding the retrieve drawer in the secure position, wherein the retrieve drawer is movable to the delivery position.

16. The apparatus according to claim 14 wherein the data store includes at least one dose record including information corresponding to a medication dose, and wherein the computer is operative to cause the first latch to cease holding the return drawer in the closed position responsive to the first user input corresponding to at least a portion of the information in the dose record.

17. The apparatus according to claim 14 wherein the first input includes data representative of a waste amount, and wherein the computer is operative responsive to the determination that the data store includes such corresponding data to include data representative of the waste amount in the data store.

* * * * *